United States Patent [19]
Mize et al.

[11] Patent Number: 6,165,795
[45] Date of Patent: Dec. 26, 2000

[54] METHODS FOR PERFORMING FIBRINOGEN ASSAYS USING DRY CHEMICAL REAGENTS CONTAINING ECARIN AND MAGNETIC PARTICLES

[75] Inventors: Patrick D. Mize; William B. Studabaker, both of Durham, N.C.

[73] Assignee: Cardiovascular Diagnostics, Inc., Raleigh, N.C.

[21] Appl. No.: 09/104,349

[22] Filed: Jun. 25, 1998

[51] Int. Cl.[7] .................................................. G01N 33/86
[52] U.S. Cl. ........................... 436/69; 436/149; 436/150; 436/164; 436/165; 436/180; 422/58; 422/73; 422/82.05; 435/4; 435/13; 73/64.41; 73/64.43; 356/39
[58] Field of Search .................................. 436/46, 63, 69, 436/149, 150, 164, 165, 180; 422/55, 58, 68.1, 73, 82.05, 82.09, 102; 73/64.41, 64.43; 356/39; 435/4, 13

[56] References Cited

U.S. PATENT DOCUMENTS

| 4,849,340 | 7/1989 | Oberhardt | 435/13 |
|---|---|---|---|
| 5,110,727 | 5/1992 | Oberhardt | 435/13 |
| 5,350,676 | 9/1994 | Oberhardt et al. | 435/13 |
| 5,453,370 | 9/1995 | Triplett et al. | 435/214 |
| 5,529,905 | 6/1996 | Lang et al. | 435/13 |
| 5,670,329 | 9/1997 | Oberhardt | 435/13 |

OTHER PUBLICATIONS

Potzsch et al. *Thrombosis Research*, vol. 86, No. 5, pp. 373–383, 1997.

Oberhardt et al. *Clinical Chemistry*, vol. 43, No. 9, pp. 1697–1702, 1997.

Nowak et al. *Seminars in Thrombosis & Hemostasis*, vol. 22, No. 2, pp. 197–202, 1996.

*Primary Examiner*—Maureen M. Wallenhorst
*Attorney, Agent, or Firm*—Oblon, Spivak, McClelland, Maier & Neustadt, P.C.

[57] ABSTRACT

A method of performing a fibrinogen assay is provided using an assay reagent containing ecarin to give an assay that is insensitive to the presence of heparin and insensitive to hematocrit, while being useful as a point of care assay in both a dry chemistry and wet chemistry format.

28 Claims, 7 Drawing Sheets

METHODS FOR PERFORMING FIBRINOGEN ASSAYS USING DRY CHEMICAL REAGENTS CONTAINING ECARIN AND MAGNETIC PARTICLES

BACKGROUND OF THE INVENTION

1. Field of the Invention

The present invention relates to methods and to analytical systems for performing fibrinogen assays using a reagent comprising ecarin in a dry chemistry or liquid chemistry format.

2. Discussion of the Background

Coagulation assays, in general, employed as clinical assays, measure the time required for the formation of a fibrin clot. Coagulation assays are principally used for screening, diagnosis, and monitoring patients receiving anticoagulant therapy.

There are many types of coagulation assays. These include: prothrombin time (PT); partial thromboplastin time (PTT); activated partial thromboplastin time (APTT); fibrinogen assay (i.e., the measurement of the concentration of clottable fibrinogen in a sample); thrombin time, also known as thrombin clotting time (TCT); activated clotting time (ACT); etc. The most frequently performed of these assays is prothrombin time.

The prothrombin time test and the activated partial thromboplastin time test are each commonly used clinical tests to determine a patient's ability to form clots. These tests, and the other tests noted above are extensively used by hospitals, clinics, and laboratories for preoperative evaluations and for anticoagulant therapy administered to cardiac patients, among other patients. These tests are each based upon time measurements, and for the most part measure what is called an end point or clotting time, which occurs when fibrinogen is polymerized to a fibrin coagulum.

The determination of the concentration of clottable fibrinogen in plasma or whole citrated blood is important for the investigation of coagulation disturbances in patients and for following (monitoring) drug therapy that affects fibrinogen. Both immunological methods and coagulation tests have been used for the determination of fibrinogen. The immunological methods display severe diagnostic disadvantages and have consequently not achieved practical importance.

In coagulation tests, the fibrinogen content is determined by the time required for coagulum (i.e. clot) formation. The most important of these methods is the method of Clauss (see *Acta Haemat.* (1957) 17: 237–246).

In the Clauss method, a diluted plasma, i.e., a weak fibrinogen solution, is mixed with a concentrated thrombin solution, the amount of thrombin being about 550 U ml$^{-1}$ of plasma. With the help of a calibration curve, the fibrinogen content of the sample is correlated to the time taken for the visible appearance of a coagulum. Coagulation tests in which one records photometrically the formation of turbidity during the course of coagulation are also known. See, e.g., Ratge et al, *Clin. Chem.* (1987) 33 (3): 420.

Finally, quantitative methods are also known in which the coagulum formed is isolated and its protein content determined. In this approach, the sample is reacted with thrombin and the coagulum formed isolated, washed and then dried. The protein content of the coagulum or its weight is then determined.

Becker et al (U.S. Pat. No. 4,692,406) disclose a method for the simultaneous determination of fibrinogen and of fibrinogen fission products in plasma. This method uses a snake venom enzyme with thrombin-like activity. In this method, the period of time between the addition of the enzyme and commencement of turbidity formation, which is a measure of the amount of fibrinogen fission products, is measured. The speed of turbidity formation is subsequently measured to determine the amount of fibrinogen present in the sample.

Many of these coagulation assays monitor change in sample optical density to measure the reaction. See, for example, Natelson et al (*Am. J Clin. Path.* (1974) 61(6): 828–833), Lipscomb (U.S. Pat. No. 4,720,787), Saito et al (U.S. Pat. No. 4,217,107), Baughman et al (U.S. Pat. No. 4,289,498), Gross et al (U.S. Pat. No. 3,458,287), Eichelberger et al (U.S. Pat. No. 4,047,890), Becker et al (U.S. Pat. No. 4,692,406), Callahan et al, "Semiquantitative Fibrinogen Determination From the PT Clotting Reaction", Tech. Bulletin Tech. THR8804, copyright 1988 by Organon Teknika, Durham, N.C., U.S.A., and Carroll et al "The Clot Signature and New Aspects in Coagulation Testing" July 1989, Ortho Diagnostic Systems Inc, Raritan, N.J., U.S.A.

In addition to being assayed by the coagulation rate method as in the Clauss method noted above, fibrinogen can be assayed by the coagulation rate as in the Clauss method modified by Vermylen et al (*Clin. Chem. Acta* (1963) 8:418–424), or by sulfite precipitation, Rampling et al (*Clin. Chem. Acta* (1976) 67:43), or by the total coagulable fibrinogen method of Ratnoff et al (*J. Lab. Clin. Med.* (1951) 37:316–320), or by an assay system based on the turbidity rate measurement of the conversion of fibrinogen to fibrin polymer sold by Du Pont (Du Pont Aca™, Du Pont Clinical Systems, Wilmington, Del. U.S.A.). The Vermylen et al method uses a glass hook or platinum loop which is continuously moved in and out of the clotting mixture until the appearance of a fibrin web indicating the end-point.

CLINICAL BACKGROUND

Today, there are 750,000 cases of acute myocardial infarction in the U.S. annually and more than one million combined cases of other arterial embolic events, pulmonary embolism (PE) and deep vein thrombosis (DVT). Approximately 25% to 35% of these cases are potential candidates for thrombolytic therapy. This therapy consists of intravenous administration of a fibrinolytic drug to promote the dissolving of the occluding blood clot. However, the therapy results in a 0.5% rate of intracranial bleeding and from 1% to 20% rate of significant extracranial bleeding. At present, no convenient, reliable and rapid diagnostic instrument is available to monitor thrombolytic therapy.

A challenge which is now emerging is how to better control thrombolytic therapy to maximize effectiveness and minimize risk of bleeding problems. Although no single diagnostic assay thus far appears to be the answer to this challenge, integration of a fibrinogen diagnostic assay with other indicators could improve therapy.

Fibrinogen measurement, while difficult to achieve at the bedside accurately and conveniently, is an important parameter in thrombolytic therapy, particularly with regard to assessment of bleeding risk and therapeutic management of bleeding once it occurs. The measurement of initial fibrinogen drop, even that associated with fibrin selective agents, such as recombinant tissue plasminogen activator (rt-PA), would also be useful confirmation that the lytic process has begun. This is equally important for other fibrin selective agents such as streptokinase, urokinase, and anistreplase, since these drugs work by means of a systemic lytic effect.

With many existing prior art methods for fibrinogen determination, centrifugation of the blood is necessary before performing the assay, because of interference from blood cells. Separation of the blood cells takes time, increasing the overall time required for the assay. These artifacts arise from the action of plasmin on a variety of proteins associated with blood coagulation including fibrinogen itself. This occurs in vitro after the blood sample has been collected. A delay of even several minutes produces inaccurate results. One solution to this problem has been to use inhibitors of plasmin or plasminogen activator as an additive to the blood collection tube to preserve the sample prior to testing. The use of inhibitors, however, adds additional expense and also restricts the field of functional assays which may be performed subsequently on the sample.

As noted supra in the past, with streptokinase, thrombin time testing had been employed to establish the presence of a lytic effect in DVT and PE where antibodies to streptokinase could neutralize a portion of the effect. A convenient, rapid, and accurate fibrinogen assay capable of being performed by the addition of one drop of whole blood to a dry chemistry test card would be a significant improvement in current diagnostic potential contribute to the optimization of thrombolytic therapy for a particular patient. In addition, the diagnostic capacity of such a system could aid in clinical trials of the many newly emerging thrombolytic drugs currently in development. There is thus a clear need for such an assay.

Therapeutic applications of the defibrinogenating agent ancrod, a purified venom component from the Malaya pit viper (*Agkistrodon rhodostoma*), include treatment of ischemic stroke, heparin replacement therapy in patients with heparin induced thrombocytopenia (HIT), unstable angina, and restenosis. Ischemic stroke is the result of blockage of blood flow in the brain caused by a blood clot or thrombus.

Fibrinogen is the natural substrate of thrombin. Thrombin cleaves both the fibrinogen peptides A and B which allows the polymerization and crosslinking of the resulting fibrin with production of a fibrin clot. Fibrinogen is also acted on by ancrod, a serine protease, which cleaves the fibrinogen peptide A, but not B. This incomplete processing produces a fibrin which polymerizes, but does not undergo crosslinking. Ancrod also possesses other protease activity and catalyzes the cleavage of additional sites on the fibrin A chain. The incomplete processing of fibrinogen and further degradation of fibrin by ancrod may result in the activation of plasminogen in vivo, which, in turn, further degrades fibrin and results in the elimination of fibrin degradation products (FDP) by the liver.

The marked reduction of fibrinogen levels causes reduced thrombus formation and lowering of blood viscosity. These two factors (along with the possible activation of the fibrinolytic cascade) increase blood flow in the area of the clot causing the ischemic stroke. This increases the likelihood of a positive outcome for the patient. Positive outcomes are associated with the marked lowering, but not complete elimination of fibrinogen (since the absence of fibrinogen could result in uncontrolled bleeding.). Thus, a point-of-care (POC) test is needed to help meter the ancrod infusion and ensure that the proper level of fibrinogen is maintained. Transportation of blood samples to a central laboratory for testing is time consuming, inhibiting the ability of the clinician to manage therapy. Transport of the sample to the central laboratory also allows time for the ancrod to further defibrinogenate the sample. This may mislead the clinician as to the amount of ancrod needed to maintain the patient in an effective treatment range. A POC type assay would allow immediate determination of fibrinogen concentration and correct adjustment of therapy.

POC tests have been disclosed using dry chemistry methods in U.S. Pat. Nos. 4,849,340; 5,110,727; 5,350,676; 5,601,991; 5,658,723; 5,670,329 and 5,677,133, the contents of which are hereby incorporated by reference. U.S. Pat. No. 5,350,676 discloses a fibrinogen test using oscillating magnetic fields and a dry chemistry reagent. U.S. Pat. No. 5,670,329 discloses a fibrinogen test using a rotating magnetic field that provides highly accurate fibrinogen measurements that are highly correlated to measurements using the Fibrometer, the "gold standard" in the industry.

Unfortunately, these methods (typically using thrombin reagents or reptilase reagents) are confounded by hematocrit. Accordingly, a POC assay is needed, using this dry chemistry type of technology, but that is not confounded by hematocrit.

SUMMARY OF THE INVENTION

Accordingly, one object of the present invention is to provide a dry chemistry based fibrinogen assay that is not confounded by hematocrit.

A further object of the present invention is to provide a fibrinogen assay using ecarin that is suitable for use in conventional Clauss type liquid assays.

A further object of the present invention is to provide a fibrinogen assay that is relatively insensitive to heparin.

A further object of the present invention is to provide a kit for performing the fibrinogen assay.

These and other objects of the present invention have been satisfied by the discovery of a method for performing a fibrinogen assay comprising:

contacting a whole blood or blood-derived sample with a fibrinogen assay reagent comprising ecarin to thereby cause formation of a fibrin clot or coagulum and correlating the formation of that fibrin clot with the content of fibrinogen in the sample, wherein the fibrinogen assay reagent can be in either a dry chemistry or liquid chemistry format, and the apparatus and reaction slides for performing such an assay.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein like reference numerals designate identical or corresponding parts throughout the several views.

DETAILED DESCRIPTION OF THE PREFERRED EMBODIMENTS

Figure 1:
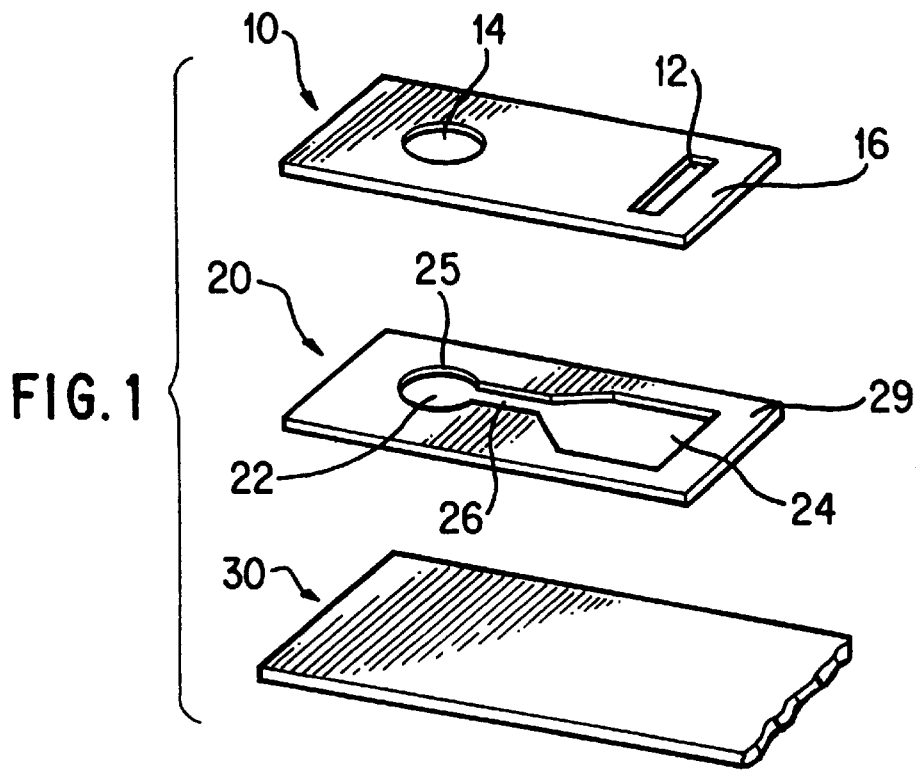
FIG. 1 is an exploded perspective of an assembled reaction slide which can be used in performing the present, end-point or kinetic, methods for measuring the clottable fibrinogen level in a blood or blood-derived sample.

There is a growing need to develop improved diagnostic approaches to aid in administration of thrombolytic therapy. Development of fast-turnaround fibrinogen measurement is one area where definite benefit to the patient could result. In addition, a simple, rapid, convenient assay of fibrinogen could have other applications outside of the thrombolytic therapy area such as: in management of post operative bleeding; in preoperative assessment; in patients with liver disease or post liver transplant patients, in disseminated intravascular coagulation (DIC) patients, in monitoring ancrod therapy of ischemic stroke and heparin induced thrombocytopenia, and as a general tool to assess bleeding at the patient's bedside. The present invention addresses and solves the drawbacks found in such current assay systems.

Hematocrit has been shown to be a confounding factor in fibrinogen assays. Hematocrit effects are minimized in Clauss-type assays by dilution of the plasma sample by 10–20 fold. The assay of the present invention provides a measurement of fibrinogen that is relatively insensitive to hematocrit. The key to this assay is the use of a reagent that acts, not directly on fibrinogen, but indirectly by way of ecarin as the reagent.

Heparin has been shown to lengthen clot times in Clauss-type assays, especially at high concentrations (>0.5 U/mL). This results in artificially low fibrinogen concentrations being calculated by conventional assays. Assay components can be adjusted to eliminate heparin effects. Another concern in fibrinogen assays is the effect of fibrinogen degradation products (FDP) in general, and specifically that the ancrod treatment will produce. FDP are known to affect Clauss-type assays so this interference may be seen in the reference method as well as the dry-chemistry method. The FDP effect can be minimized by choosing the correct clotting enzyme. Fibrinogen structure may differ from person to person and affect the apparent fibrinogen concentrations in different assays.

The present invention provides a novel fibrinogen assay using ecarin as the assay reagent and based on monitoring the movement of magnetic particles incorporated in the assay reaction. Ecarin, a protein prothrombin activator from *Echis carinatus* venom (E.C. 3.4.99.27), was isolated by Kornalik et al in 1969. Ecarin causes coagulation of citrated whole blood or plasma by the calcium-independent activation of prothrombin. Ecarin has been characterized by Morita et al and by Kornalik and Blomback as a single chain glycoprotein with a molecular weight of 55–60 Kdaltons which exerts metalloproteinase activity inhibited by EDTA, gluthaione, cysteine, and mercaptoethanol. Common serine proteinase inhibitors such as diisopropyl-fluorophosphate (DFP), soy bean trypsin inhibitor (SBTI), ovomucoid and aprotinin do not inactivate ecarin.

Ecarin catalyzes the hydrolytic cleavage of the 323 Arg-324Ile bond in the human prothrombin molecule, whereby thrombin activity is generated without the release of any zymogen fragment. This form of active prothrombin has been termed meizothrombin. Meizothrombin is not inhibited by the heparin-ATIII complex. Meizothrombin acts on fibrinogen to form a clot in the fibrinogen assay.

The use of ecarin in the present fibrinogen assay is beneficial because:

1. Ecarin and meizothrombin are not inhibited by heparin, which is a common anticoagulant. Heparin does confound the results of many commercial assays that use the clotting agent thrombin, which acts directly on fibrinogen.
2. Ecarin generates meizothrombin throughout the entire assay, which increases the differentiation between the A/B (vide infra) values for clinical samples containing low (20–100 mg/dl) and high (200–300 mg/dl) levels of fibrinogen.
3. The ecarin based assays of the present invention have an increased sensitivity to fibrinogen, increased reproducibility, and increased dynamic range, compared to many commercial assays.

As noted above, in the present assay, a dry reagent matrix in which is embedded a plurality of magnetic particles, distributed homogeneously therethrough, is subjected to an oscillating or rotating magnetic field, preferably an oscillating magnetic field. The oscillating or rotating magnetic field may be obtained in accordance with either of U.S. Pat. Nos. 5,350,676 or 5,670,329 previously incorporated by reference.

The whole blood or blood-derived sample is then added to the reagent, causing it to become solubilized, thereby freeing the particles to move in an oscillating pattern induced by the oscillating magnetic field. As discussed in detail in U.S. Pat. No. 5,110,727, under the influence of the magnetic field, the freed magnetic particles form columnar structures or stacks, which, under the influence of the oscillating magnetic field, create a flicker phenomena due to a change in the orientation of these columnar structures or stacks.

The oscillation of the particles is optically monitored by subjecting the particles to incident light and detecting reflected (scattered) light rays. Before the sample is added to the dry reagent matrix, the magnetic particles which are entrapped in the dry reagent matrix are incapable of oscillation. After the magnetic particles are freed by addition of the sample to the dry reagent matrix, a maximum number of particle-based columnar structures or stacks can quickly be observed to oscillate to the greatest degree, providing a maximum oscillation amplitude, shown as A in FIG. 3. As the reaction progresses, a coagulum forms restricting the degree of oscillation of an increasing number of particle-based columnar structures or stacks. This gradual decrease in the flicker pattern produces a residual post-peak minimum amplitude, shown as B in FIG. 3.

In the present assay, either the degree of particle movement relative to said oscillating magnetic field is monitored to measure the start time and stop time of the assay, or one or more features of the kinetic curve, other than clotting time, is/are used to measure fibrinogen concentration in the sample.

In the present blood coagulation monitoring system, it is thought that higher fibrinogen levels produce fibrin clots which restrict particle oscillation to a greater degree thereby resulting in a lower minimum oscillation signal after the peak signal. As may be seen in FIG. 4, the clotting curve is complex. Starting at 1, the first indication of particle oscillation is apparent. The magnitude of magnetic particle oscillation is apparent. The magnitude of magnetic particle oscillation as monitored optically increases from the start of the assay at 1 to the peaks at 2 and 2' on the upper and lower portions of the wave envelope, respectively.

Figure 4:
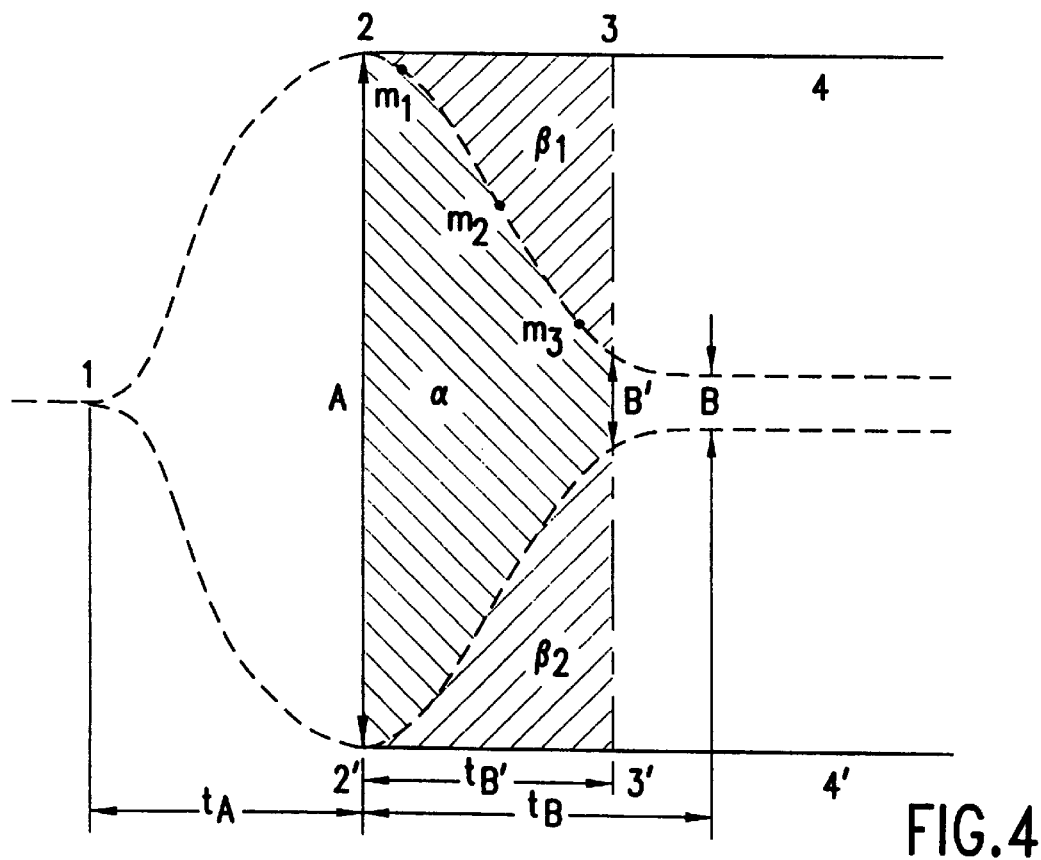
FIG. 4 shows additional features of the kinetic clotting waveform which may be utilized as parameters to construct specific algorithms to measure fibrinogen.

The oscillation signal amplitude at the peak is designated as A and shown in FIG. 4 as a signal difference between 2 and 2'. The time at which A occurs, $t_A$, is the clotting time. Tracing along the waveform envelope at the top, the amplitude decreases after $t_A$.

Three points $m_1$, $m_2$, and $m_3$ are shown. Points $m_1$ and $m_3$ are chosen at arbitrary but fixed times. Point $m_2$ is chosen as an inflection point. The slope of the curve taken at $m_1$, $m_2$ or m3 can be utilized as a measure of fibrinogen, since these slopes are steepest (most negative) at the highest fibrinogen levels and become less steep with decreasing fibrinogen.

After $m_3$, the oscillation signal amplitude continues to decrease with increasing time, eventually approaching an asymptotic value B. Fibrinogen concentration is proportional to A/B and to (A−B)/A. Fibrinogen concentration is also inversely proportional to B and directly proportional to A−B, but these parameters alone are generally less precise than A/B or (A−B)/A.

Other, more precise, measures of fibrinogen concentration are areas obtained by integrating portions of the kinetic curve. For example, the area bounded by: a straight line extending between 2 and 2' of length or amplitude A at the left; amplitude B' at the right (where: B' is the amplitude of the curve at the time $t_{B'}$; and $t_{B'}$ is taken typically at a time between 10 seconds after $t_A$ and up to 90% of $t_B$ but more typically at 60% of $t_B$) and the area defined by the waveform envelope at the top and bottom is designated as alpha and is inversely proportional to fibrinogen concentration in the sample.

Another area, designated as β may be utilized. β is equal to the area of the rectangle with sides of magnitude A and opposite sides of magnitude $t_B$, minus the area designated as α. β is shown in FIG. 4 as consisting of two portions: an upper portion, $β_1$ and a lower portion, $β_2$. The line extending through amplitude B' and intersecting parallel lines 4 and 4' constructed as perpendiculars to the line of magnitude A at points 2 and 2° helps to define the right boundary of β. β is directly proportional to fibrinogen concentration and is very precise.

β and a may also be used in combination, i.e., taken as a ratio or difference to indicate fibrinogen level. In addition α and/or β could be calculated independently of time, for example by always using $t_B$ as the horizontal measure for area calculation (see FIG. 4).

Figure 5:
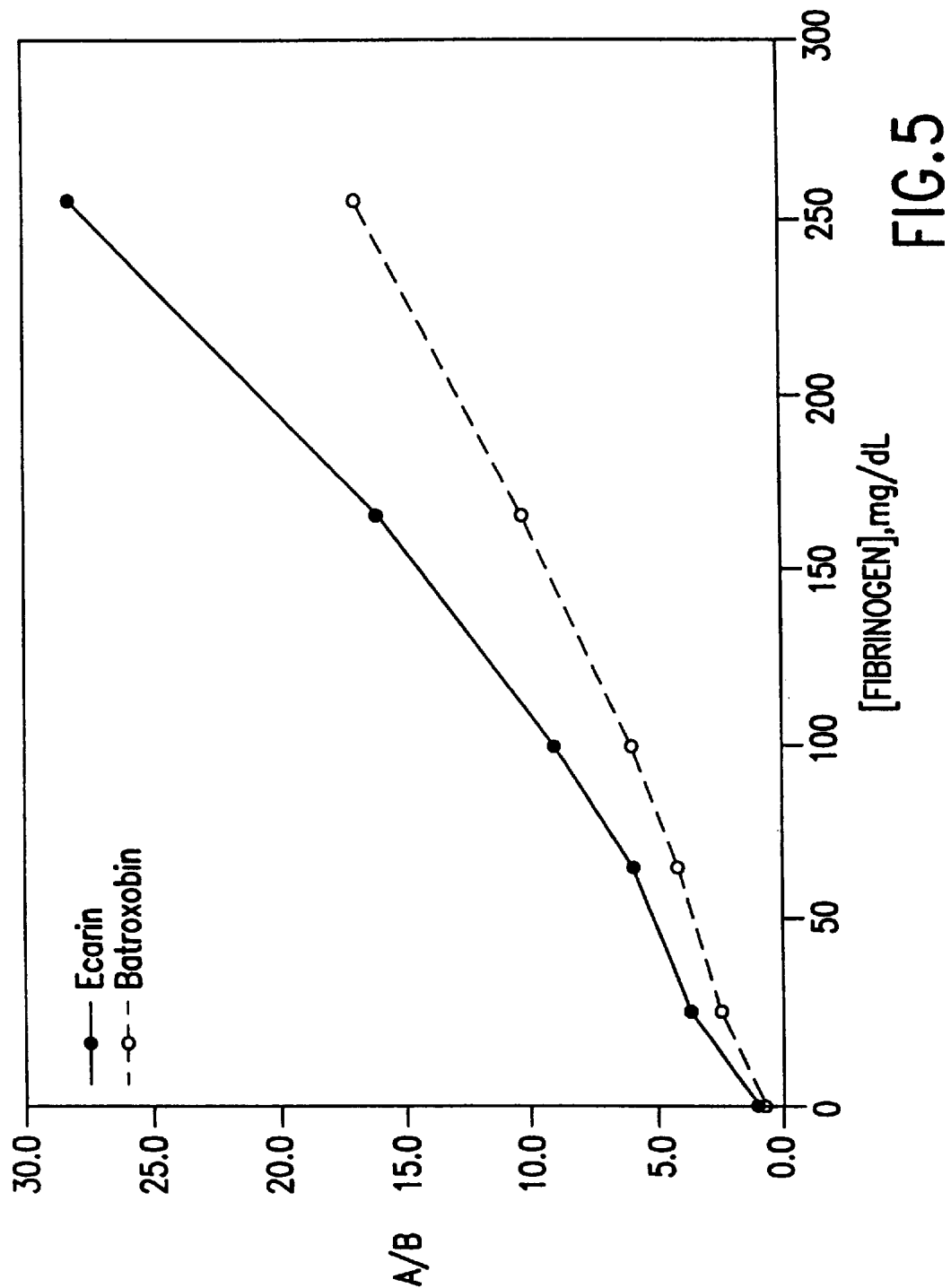
FIG. 5 shows a comparison of the A/B ratios for an ecarin assay versus a batroxobin assay.

FIG. 5 shows how some of the kinetic parameters of the clotting curve vary with concentration of fibrinogen for a dry reagent slide incorporating reptilase and a citrated plasma sample consisting of pooled normal plasma diluted in varying amounts in fibrinogen deficient plasma.

The present invention thus provides fibrinogen measurement using magnetic particle dry chemistry technology. Using this approach fibrinogen can be measured with each of the approaches listed below.

Although a capillary slide geometry, such as that of the reaction slide described in any of U.S. Pat. Nos. 4,849,340; 5,110,727; 5,350,676; 5,601,991; 5,658,723; 5,670,329 or 5,677,133, all of which incorporated by reference above, is ideally suited for creating a properly patterned format, housing the reagent, and monitoring the sample, the assay of the present invention will work perfectly well by simply adding a premeasured amount of dry reagent containing magnetic particles to any solid surface (e.g., a microtiter plate well or substantially flat surface). Although the preferred embodiment of the technology is a dry-chemistry format, the assay using ecarin can also be performed in a liquid chemistry format on a conventional laboratory analyzer, such as the "Fibrometer", the gold standard fibrinogen analyzer in the industry, or the Thrombolyzer (commercially available from Organon Teknika).

It is important that the dry reagent be prepared such that it is rapidly dissolved upon the addition of the blood or blood-derived sample. Freeze-drying on a surface, or even better, between two surfaces closely apposed at a capillary or near capillary distance works best. This produces a mass of low matter content which enables rapid sample penetration and dissolution.

Although freeze drying provides excellent results for preparation of the dry magnetic particle-containing reagent, room temperature, vacuum, desiccant, convective, or other types of drying can also be used to achieve good results. For example, room temperature drying of reagent on the base of a reaction slide (with spacer in place) followed by attachment of the cover can be used to obtain a self-metering dry reagent containing element.

Figure 2:
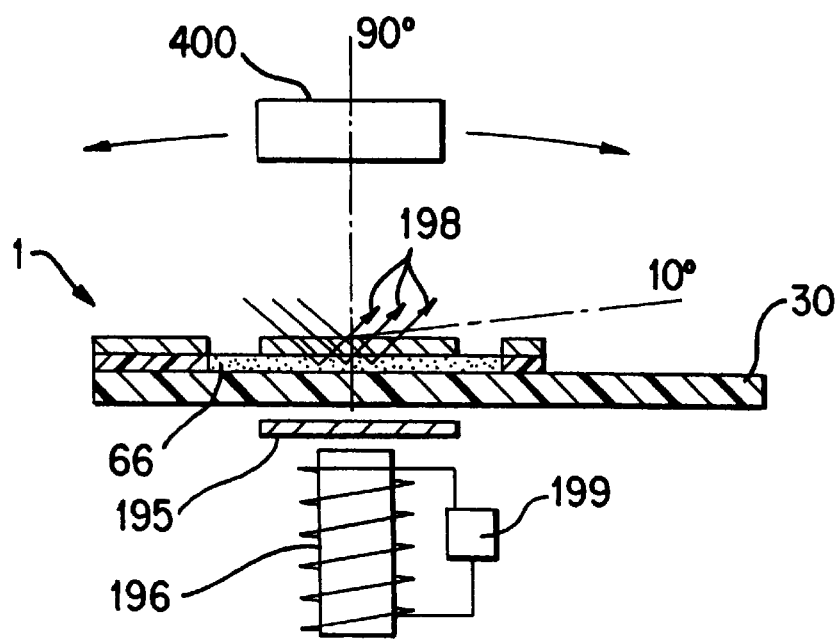
FIG. 2 is a longitudinal vertical cross-section of a reaction slide together with apparatus for using magnetic particles to measure the reaction.

In a preferred embodiment the reaction slide illustrated in FIGS. 1 and 2 is used. FIG. 1 is an exploded view showing the relative position of the cover (10), overlay (20) and base (30) components of the slide. Cover (10) comprises a thin glass or polymer sheet transparent to light, having formed therein a sample receiving opening (14) and an elongate opening (12) proximate to distal end (16) of the cover.

Overlay (20) comprises a thin glass or polymer sheet, typically transparent, having formed therein a cut-out, the cut-out having a geometry essentially as shown to form a sample well (22), a reaction chamber (24) and an optional conduit (26) communicating the reaction space and the sample receiving opening.

Thus the cut-out of overlay (20) can either have a geometry forming sample well (22) and reaction chamber (24) in communication with each other, or a geometry comprising sample well (22), reaction chamber (24), and conduit (26) essentially as shown.

The reaction chamber (24) defines a reaction volume upon assembly of the cover, overlay and base. Advantageously, tapering walls (25) form a transition between conduit (26) and sample well (22) or if conduit (26) is not used, and reaction chamber (24). The distal end of the overlay is closed as shown at (29).

The base (30) comprises a sheet of glass or polymer material, which is typically somewhat thicker than either the cover (10) or overlay (20).

As shown in the figure, the length (left to right in the drawing) of cover (10) is approximately the same as that of overlay (20), and the width (top to bottom in the drawing) of cover (10) and overlay (20) are about the same and typically less than that of base (30). When the cover, overlay and base are assembled, the bottom surface of cover (10), facing base (30), is spaced from the top surface of base (30) by a distance that is sufficiently small to cause a volume of sample corresponding to the volume of the reaction chamber to be drawn simultaneously into the reaction volume by capillary action. This action is made possible by the presence of vent (12). In use, reaction chamber (24) is charged with the dry reagent containing magnetic particles homogeneously dispersed therethrough.

In one embodiment of the present invention, the reaction slide has a sample well for receiving a liquid sample, a reaction chamber and a conduit means situated between the sample well and the reaction chamber and being in fluid communication therewith. The conduit means contains a dry reagent matrix comprising ecarin in which is embedded a plurality of magnetic particles distributed homogeneously therethruogh, wherein the dry reagent is present only in the conduit. As an additional step, one can add a volume of distilled water to the sample well, prior to addition of the whole blood or blood-derived sample, wherein the volume of distilled water is sufficient to be taken into the conduit via capillary action, thereby solubilizing the dry reagent and freeing the magnetic particles prior to addition of the whole blood or blood-derived sample.

FIG. 2 provides a longitudinal vertical cross-section of the reaction slide together with an apparatus for using the magnetic particles to measure the assay. In this figure, reaction slide 1 is disposed and in close proximity to a permanent magnet (195). Beneath the permanent magnet (195) is an electromagnet (196) which is driven by power supply (199) for cycling voltage on and off at a desired frequency. In the practice of the present invention it is possible to use the permanent magnet above (without the electromagnet), creating an oscillating magnetic field with the permanent magnet by moving the permanent magnet back and forth along a plane essentially parallel to the plane of the reaction slide. In another embodiment the electromagnet above is used to generate an oscillating magnetic field. In still another embodiment, both of these magnets are used essentially as shown in FIG. 2.

A light source such as an infrared or near-infrared light emitting diode is appropriately situated for providing incident light on the reaction chamber and a detector or sensor positioned for detecting light rays reflected from the sample within the reaction volume (66). The reflected rays, depicted as arrows (198), are detected by detector (400). Detector (400) can be positioned at any position which will permit it to detect the reflected (scattered) rays, but a position between the 90° and the 10° position, inclusively, is preferable, with a position between the 90° and 45° position being preferred, and between 90° and 75° being most preferred.

Clot Formation Kinetic Approaches

Along with buffers sufficient to control pH in the ranges known in the art (typically 6.5 to 8.0), the reagent used in this assay contains ecarin in an amount sufficient to cause coagulation of normal plasma or whole citrated blood with near minimal B values plus magnetic particles, typically 8.3 mg ml$^{-1}$ but variable over a wide range (see U.S. Pat. No. 5,110,727). The blood sample does not normally require dilution and may be added directly to the dry chemistry assay mixture. Some dilution, to within 1:2 (by volume) and most preferably not more than 1:4 (by volume) is, however, possible with this embodiment, and may be used if desired. In some cases, dilutions as great as 1:10 (by volume) or even 1:20 (by volume) could be employed advantageously, for example at very high fibrinogen levels.

For this reason the exact amounts of the various clotting reagents employed in formulating suitable dry reagents for use in combination with magnetic particles cannot be specified, but rather the quantities of these clotting reagents are determined functionally as described for each embodiment. The buffer type and concentration may be less important than the pH. Buffers which are commonly employed in blood coagulation reactions may generally be used. Owrens, HEPES, and Tris are among these, with HEPES being preferred.

In the present invention the dry-chemistry formulation preferably contains ecarin, with optional components present such as a fibrin polymerization inhibitor, calcium, one or more buffers, and/or one or more stabilizers. The components can be used in concentrations preferably as follows: (concentrations described are final assay concentrations after addition of sample and reconstitution of the dry-chemistry reagent):

Ecarin or other prothrombin activator—0.1 to 5.0 U/mL, preferably from 0.4 to 1.6 U/mL, most preferably at about 0.8 U/mL.

Fibrin polymerization inhibitor, preferably Gly-Pro-Arg-Pro—1.0 to 1000 ug/mL, preferably from 5 to 100 ug/mL, most preferably at about 25 ug/mL.

Calcium—1.0 to 12.5 mM, preferably from 1.0 to 6.0 mM, most preferably at about 3.0 mM.

Paramagnetic Iron Oxide Particles (PIOP)—1.0 mg/mL to 50 mg/mL, preferably from 3 to 15 mg/mL, most preferably at about 8.3 mg/mL.

One or more additives and/or stabilizers for lyophilization including polyethyleneglycol (PEG) from 500–50,000 MW, saccharides including lactose, maltose, sucrose or the like from 1 to 1000 mg/mL, bovine serum albumin (BSA) from 0.1–10 mg/mL.

One or more buffers to maintain pH from 6.5 to 8.0, preferably from 7.0 to 8.0, most preferably at about 7.8. The buffers can be any conventional buffer suitable for use with blood products, particularly those listed above.

Other factors can affect performance, for example additives such as those enumerated above. Furthermore, optimum pH and buffer selection may depend somewhat upon the particular lot of reagent chosen. It is also expedient to use certain additives to improve dissolution characteristics of the dry reagent and to better disperse the magnetic particles upon solubilization. The exact amounts may depend upon the properties of the clotting reagent and may differ with each lot number. Within the framework described herein, the optimization of these variables is within the ability of one of ordinary skill in the art.

Figure 3:
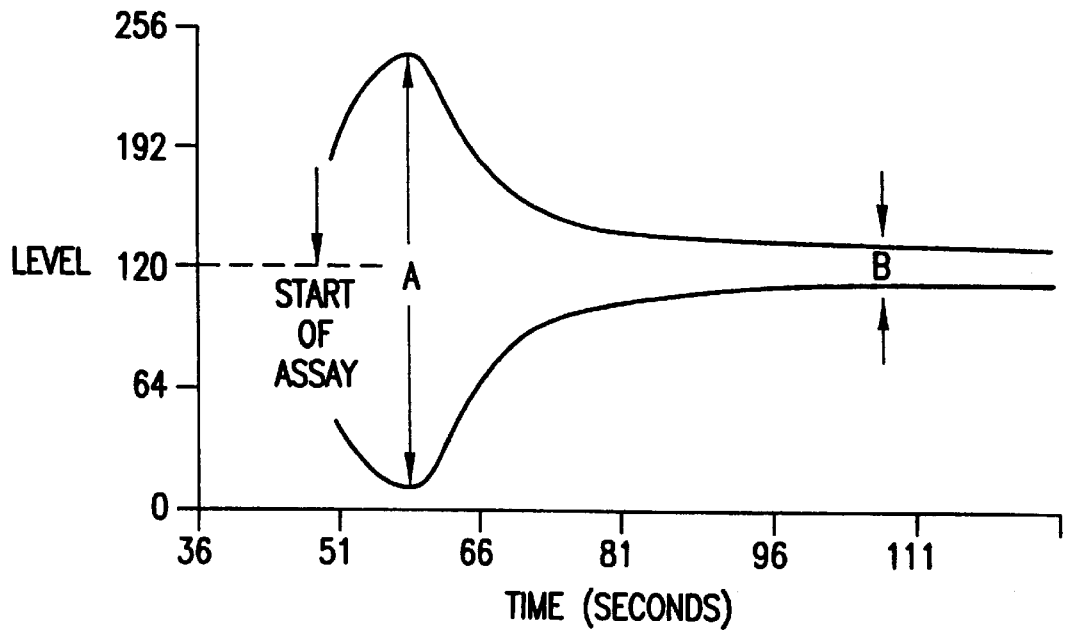
FIG. 3 illustrates the clotting curve for the fibrinogen assay, with A designating the maximum amplitude of particle oscillation and B designating the subsequent residual post peak minimum amplitude of particle oscillation.

To measure fibrinogen using the clot formation kinetics, clotting time is preferably not used. Instead, kinetic parameters reflecting features in the clotting curve (shown FIGS. 3 and 4) are utilized. In FIG. 3, A is the peak height maximum (maximum oscillation amplitude), B is the minimum (residual post peak minimum) which is observed after A is reached.

Either A and B, or B only, are used to determine a factor proportional to fibrinogen concentration in the sample. The following measures may be employed: (i) B alone; (ii) A/B (or B/A ); (iii) A–B; or (iv) (A–B)/A or A/(A–B). Alternatively, (v), as may be seen in FIG. 4, the negative slope (e.g., at or near the inflection point) between A and B can be utilized. Yet another alternative, (vi), as may be seen in FIG. 4 is the area enclosed by the clotting curve. This area may be bounded by vertical axes at the peak (A) and at a set time after A, e.g., 45 seconds, where: A is normalized and thus made equivalent for each separate assay curve.

Clotting Time Approaches (Clauss Type)

Along with buffers in amounts sufficient to control pH the reagent used contains ecarin in a concentration sufficient to cause coagulation of normal plasma or whole citrated blood with B values somewhat above the absolute minimum obtained at ever increasing ecarin concentration and the magnetic particle concentration is typically 8.3 mg ml$^{-1}$, but can be varied over a wide range (see U.S. Pat. No. 5,110, 727). In this embodiment the blood sample to be analyzed is first diluted with a buffer-substrate combination. The buffer may be any conventional buffer, preferably Owrens buffer, HEPES, or TRIS. The substrate for ecarin is prothrombin (1 U/mL). The diluted sample is then added to the dry chemistry assay mixture in an appropriate analyzer. Clotting time is then measured.

For the Clauss type methods (clotting time based) dilution of the sample is necessary to achieve sufficient dynamic range, as discussed by Vermylen et al. *Clin. Chim. Acta*, (1963) 8: 418–424. In the present system, this is achieved by sample predilution.

Fibrinogen Screening Tests (Clotting Time Based)

The reagents used in this embodiment contain ecarin, along with buffers and/or stabilizers. The blood sample should not be diluted and is added directly to the dry chemistry mixture. Clotting time is then measured. These screening tests are generally useful to determine that fibrinogen is abnormal.

In a first (kinetic) preferred embodiment, the present method for measuring the clottable fibrinogen level in a blood or blood-derived sample (performing a fibrinogen assay) comprises the following steps (i) to (iv).

(i) Subjecting to an oscillating or rotating magnetic field a reaction slide bearing (1) a sample well for receiving a liquid sample and (2) a reaction chamber containing a dry reagent matrix comprising ecarin in which is embedded a plurality of magnetic particles distributed homogeneously throughout the reagent matrix.

(ii) Adding a whole blood or blood-derived sample to the sample well whereby the sample is introduced simultaneously to the reaction chamber, the reagent is solubilized and the particles are freed to move in response to the magnetic field, (iii) Optically monitoring the reaction chamber to measure the maximum amplitude of particle oscillation, A, and the subsequent residual post peak minimum amplitude, B, of the particle oscillation, (iv) Using at least B, or an area defined by the kinetic clotting curve between A and B to measure fibrinogen concentration in the sample.

FIG. 5 shows a response curve for A/B versus fibrinogen concentration for an ecarin based fibrinogen assay.

In a second (end-point) preferred embodiment the method of performing a fibrinogen assay comprises the following steps (i') to (iv').

(i') Subjecting to an oscillating or rotating magnetic field a reaction slide bearing (1) a sample well for receiving a liquid sample and (2) a reaction chamber containing a dry reagent matrix comprising ecarin, in which is embedded a plurality of magnetic particles distributed homogeneously throughout the reagent matrix, wherein sample well and reaction chamber are in fluid connection through a transport zone of geometry such that a volume of liquid analyte sample placed in the sample well and corresponding to the volume of said reaction chamber is spontaneously transported from said sample well to said reaction chamber, (ii') Adding a whole blood or blood-derived sample (e.g., 2 to 20 fold diluted (by volume) in HEPES buffer and prothrombin) to the sample well whereby the sample is introduced spontaneously to the reaction chamber, the reagent is solubilized and the particles are freed to move in response to the magnetic field, (iii') Optically monitoring the reaction chamber to measure a start time and a stop time for the fibrinogen assay, corresponding to a change in the degree of particle movement relative to said magnetic field, (iv') Using the start time and the stop time to measure fibrinogen concentration in the sample.

It should be recognized that the first embodiment, which is based on clot formation kinetics, could typically utilize a lower concentration of clot forming reagent than the second embodiment which is based on clotting time. The exact concentrations of reagents employed however, would vary with the type and potency as noted supra. Further, the second embodiment would tend to have a narrower range of utility, since the results would become less reliable at lower fibrinogen concentrations.

Yet another embodiment is to use a reagent concentration comparable to that in the first embodiment but to measure clotting time, as in the second embodiment, on an undiluted sample, instead of clot kinetic parameters (as in the first embodiment). This approach provides a quantitative screening test which is sensitive over the most clinically useful range of fibrinogen levels (low normal to below normal) and can be useful in rapid assessment of fibrinogen abnormalities from an undiluted whole blood or plasma sample. This embodiment provides results analogous to a thrombin time, reptilase time, or equivalent test or a fibrinogen value when used with a standard curve for interpretation. Use of a plot of fibrinogen vs. inverse clotting time (1/clotting time) is known in the art.

Having generally described this invention, a further understanding can be obtained by reference to certain specific examples which are provided herein for purposes of illustration only and are not intended to be limiting unless otherwise specified.

EXAMPLES

Dry-chemistry reaction slides for fibrinogen detection using ecarin or batroxobin were made by the following general procedure:

25 uL of a solution containing 0.8 U/mL ecarin (PentaPharm) or 3.0 U/mL batroxobin (PentaPharm), 3.0 mM calcium chloride (Aldrich Chemical Company), 50 mM HEPES, pH 7.8, 8.3 mg/mL PIOP, with appropriate additives and stabilizers were injected into an assembled reaction slide device (as in FIG. 1), frozen, and lyophilized to yield the dry-chemistry formulations.

The reaction slides were placed in the TAS (Thrombolytic Assessment System) analyzer, an instrument for measuring paramagnetic particle movement (commercially available from Cardiovascular Diagnostics, Inc., and described in U.S. Pat. No. 5,110,727), and to the reaction slide card was added 30 uL of plasma, citrated whole blood, or blood derived sample. The TAS analyzer was programmed to detect clot-type waveforms and A/B ratios. In addition, waveforms were recorded electronically for subsequent analysis.

Frozen pooled human plasma (FACT, 250 mg/dL fibrinogen, Helena Laboratories) and a human plasma sample naturally deficient in fibrinogen (<15 mg/dL) were thawed at 37° C. and kept at ambient temperature. FACT and fibrinogen deficient plasma were diluted together to yield plasma samples of 0, 20, 40, 60, 80, and 100% FACT content. 30 uL of each sample was added to a reaction slide, in the TAS analyzer, and the clotting time and A/B ratio determined.

FIG. 5 shows a comparison of the A/B response of the ecarin and batroxobin dry-chemistry assays for plasma samples containing different levels of fibrinogen. The ecarin-based fibrinogen assay shows greater linearity and uniform response in inverse clotting time than the batroxobin-based fibrinogen assay.

Figure 6:
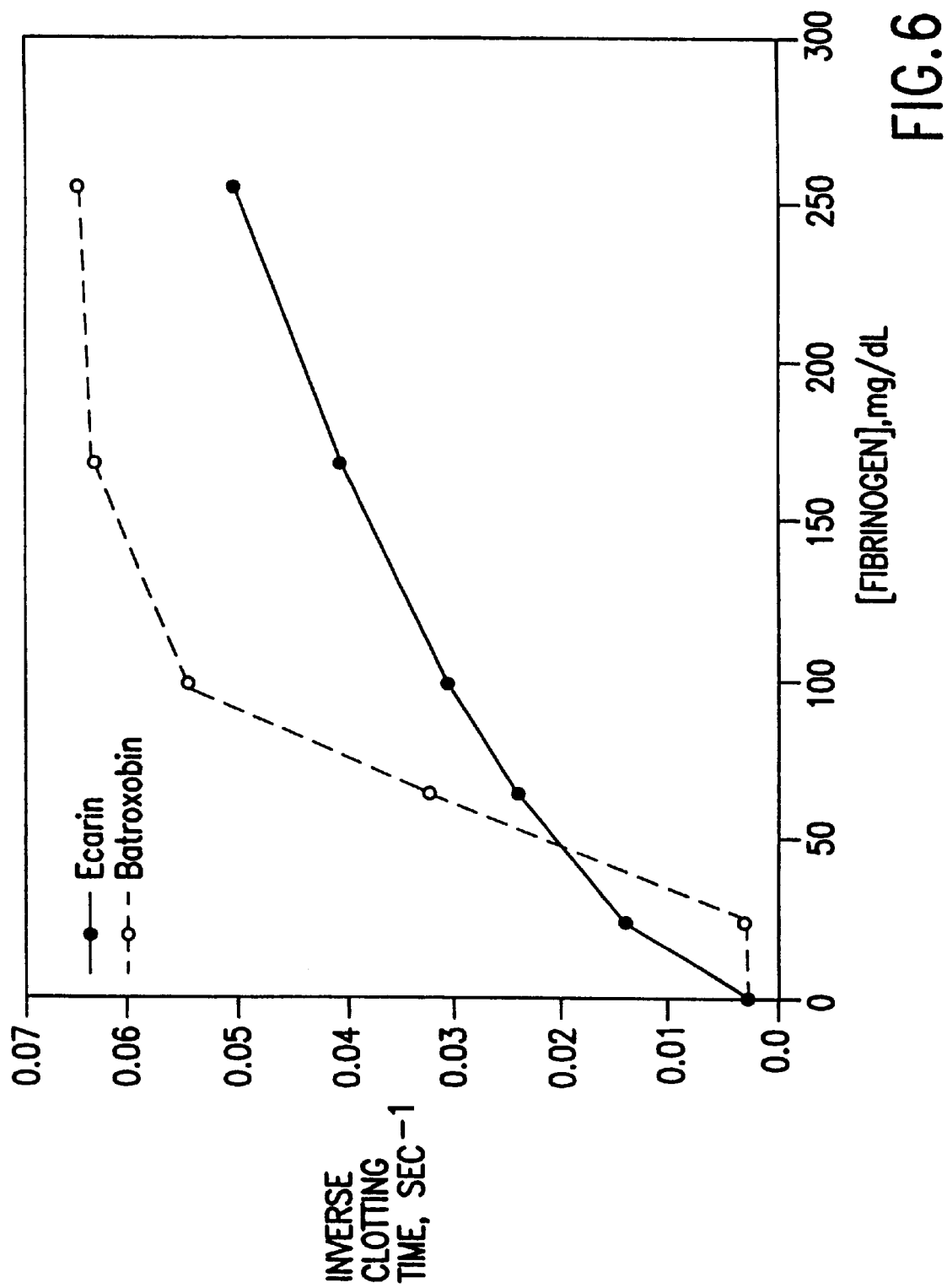
FIG. 6 shows a comparison of the inverse clotting time response of ecarin and batroxobin dry-chemistry assays for plasma samples containing different levels of fibrinogen.

FIGS. 5 and 6 illustrate the significant advantage in sensitivity and dynamic range when using ecarin, as compared to batroxobin, as the activating enzyme.

Liquid Ecarin-Based Fibrinogen Assay

Whole citrated blood was centrifuged at 1500 rpm for 15 minutes. Plasma was removed from the packed red blood cells and discarded. Packed red blood cells were added in a 1:1 dilution with the plasma samples prepared above to yield whole citrated blood samples with different fibrinogen concentrations. These citrated blood samples with different levels of fibrinogen were diluted 1:1 with the dilution buffer described below. 50 µL of the diluted sample and 50 µL of an ecarin-based liquid reagent were combined in a reaction cell in a STAGO ST4 coagulation analyzer and clotting time recorded.

Figure 7:
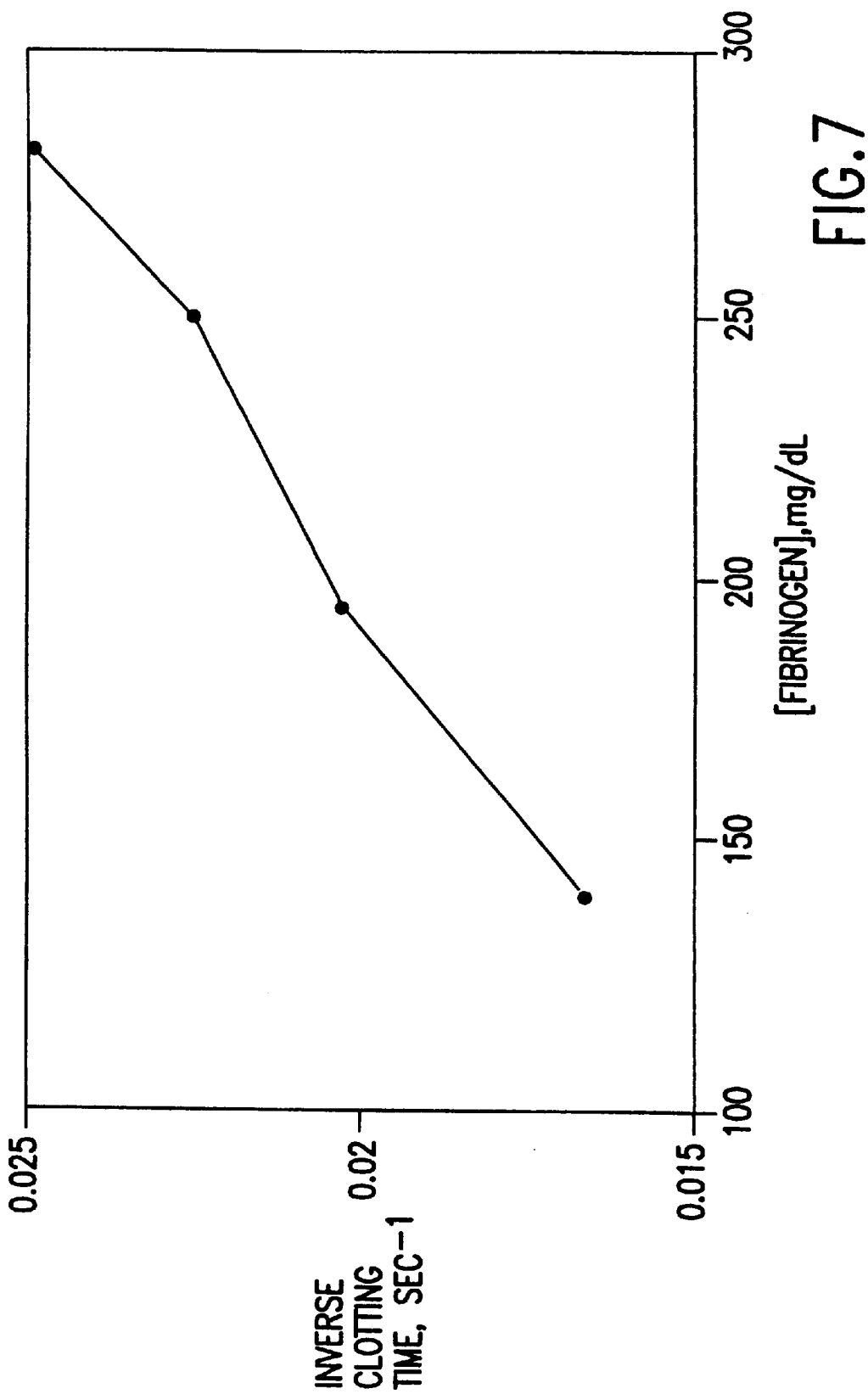
FIG. 7 shows the inverse clotting time response of the liquid-based ecarin assay.

FIG. 7 shows the inverse clotting time response of the liquid-based ecarin assay. Data shows good linearity for the fibrinogen levels tested.

The dilution reagent for preparing diluted blood or plasma samples (blood derived samples) in the above examples was principally 50 mM HEPES buffer, calcium 3.0 mM, pH 7.8 and 1.0 U/mL prothrombin (ecarin substrate). Blood or plasma sample could be diluted 1:1 to 1:20 with dilution buffer.

Blood (centrifuged to yield plasma) and plasma samples prepared above were also tested on a SYSMEX CA 1000 coagulation analyzer in a modified Clauss Assay (Dade Thrombin reagent, Dade-Behring) to determine reference fibrinogen values.

Clinical Samples and Protocols

Clauss method: A modified Clauss Method (Fiblastin™, Organon Teknika) was used as the reference method. Citrated plasma was isolated from blood by centrifugation and plasma mixed with Fiblastin™ (thrombin) reagent. Clotting time was measured using a Thrombolyzer (Organon Teknika).

Dry-chemistry fibrinogen test: Dry chemistry reaction slides were prepared as described above and were formulated as in the preferred embodiment.

PATIENT TESTING: Twelve healthy volunteers received 1 U/Kg of ancrod as a single infusion over a six-hour period. Citrated whole blood samples from each individual were collected prior to the start of infusion and at intervals during and up to 72 hours after the start of infusion. Each sample was analyzed in duplicate using the ecarin-based fibrinogen reaction slides, the batroxobin-based reaction slides and by the reference method. The hematocrit of each sample was also measured.

Figure 8:
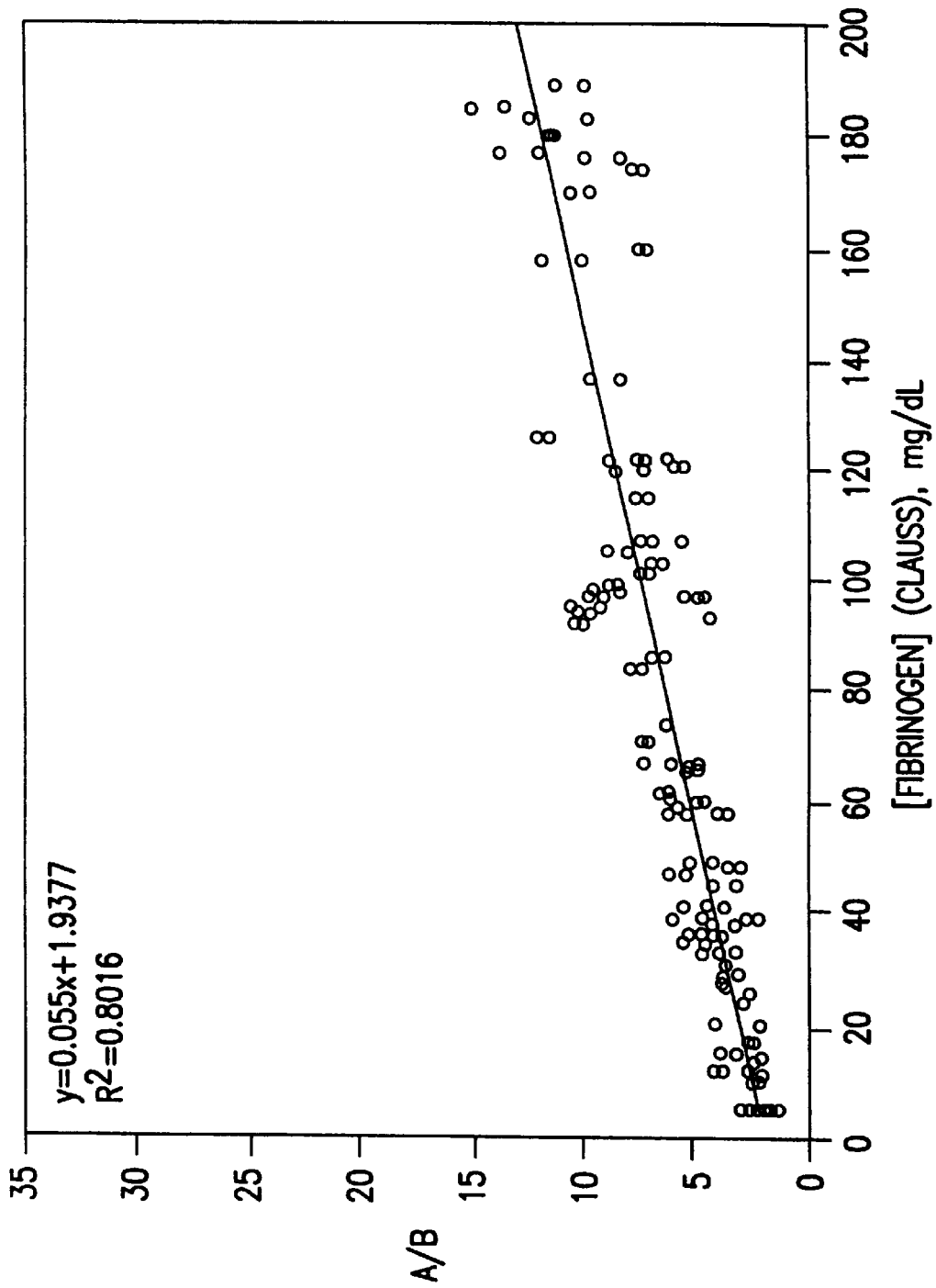
FIG. 8 shows the dose-response curve using A/B to measure response with a dry chemistry batroxobin-based assay.
Figure 9:
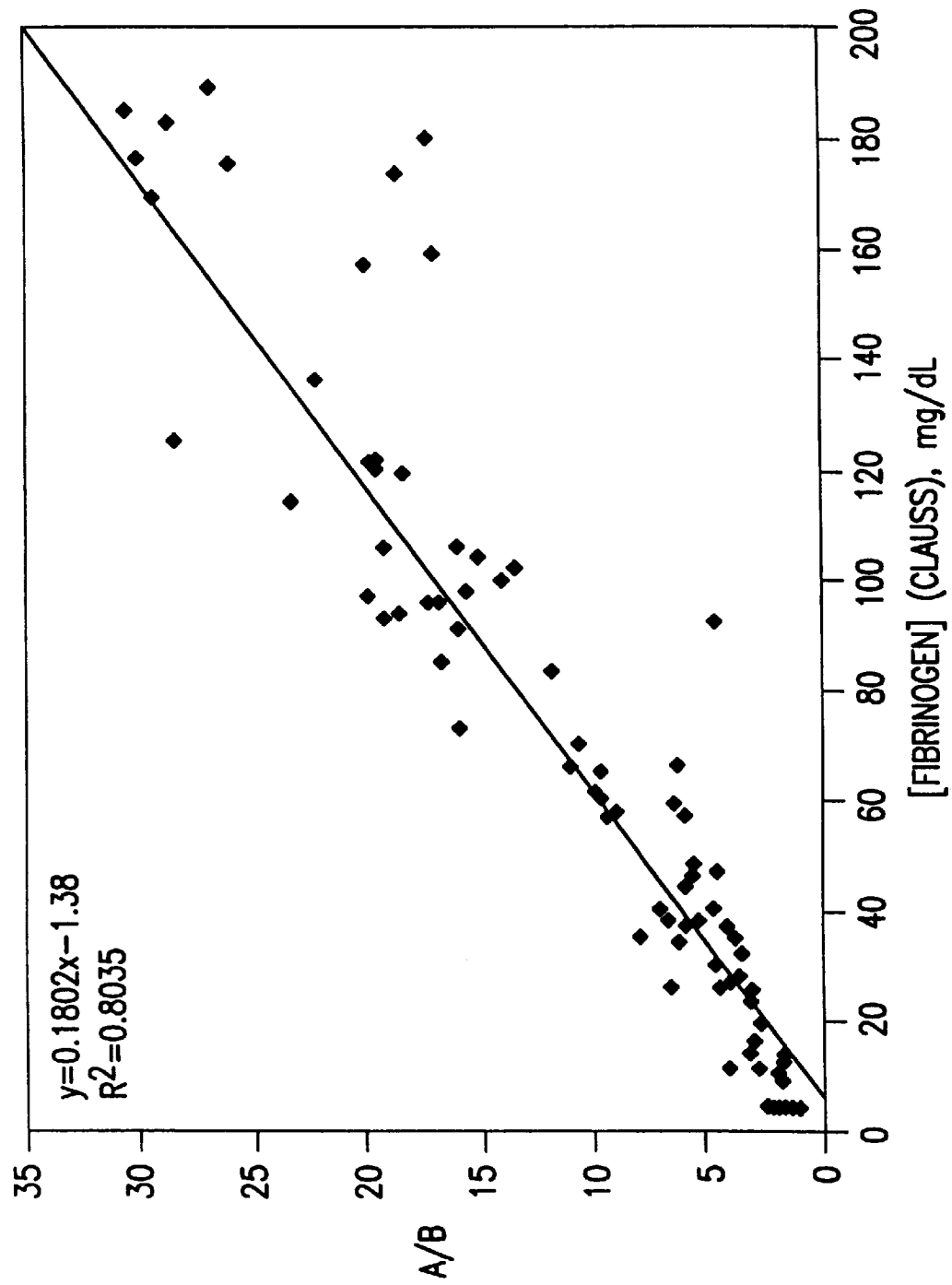
FIG. 9 shows the dose-response curve using A/B to measure response with a dry chemistry ecarin based assay.

FIGS. 8 and 9 show the dose-response curves for the measurement of fibrinogen in citrated whole blood using A/B to measure response with batroxobin-based and ecarin-based assays. Comparison of FIGS. 8 and 9 reveals the significantly greater sensitivity of the reaction slides containing ecarin. Furthermore, sample hematocrit ranged from 35% to 47%. The good correlation illustrated in FIG. 9 demonstrates a minimal hematocrit effect on assay performance.

Obviously, additional modifications and variations of the present invention are possible in light of the above teachings. It is therefore to be understood that within the scope of the appended claims, the invention may be practiced otherwise than as specifically described herein.

What is claimed is:

1. A method of performing a fibrinogen assay, comprising:
   (i) subjecting to an oscillating magnetic field a reaction slide bearing (1) a sample well for receiving a liquid sample and (2) a reaction chamber containing a dry reagent matrix comprising ecarin in which is embedded a plurality of magnetic particles distributed homogeneously therethrough;
   said sample well and reaction chamber being in fluid connection through a transport zone of geometry such that a volume of liquid analyte sample placed in said sample well and corresponding to the volume of said reaction chamber is transported from said sample well to said reaction chamber;
   (ii) under conditions suitable for conducting a fibrinogen assay, adding a whole blood or a blood-derived sample to said sample well whereby said sample is introduced into said reaction chamber, said reagent is solubilized and said particles are freed to move in an oscillating pattern induced by said oscillating magnetic field, wherein said oscillating pattern has a start time and a stop time, corresponding to a change in the degree of particle movement relative to said oscillating magnetic field;
   (iii) optically monitoring said reaction chamber to provide a particle oscillation curve and to measure one or more of the following parameters (iiia) said start time and said stop time for said fibrinogen assay, or (iiib) a maximum amplitude of said particle oscillation, A, and a subsequent residual, post peak minimum amplitude, B, of said particle oscillation, or (iiic) a slope of said particle oscillation curve or area defined by said curve in the region between A and B; and
   (iv) using said start time and said stop time, or at least B, or said slope, or said area to correlate at least one of said parameters (iiia)–(iiic) to the concentration of clottable fibrinogen in standard samples to measure the concentration of clottable fibrinogen in said whole blood or blood-derived sample.

2. The method of claim 1, wherein said dry reagent further comprises at least one member selected from the group consisting of buffers and binding agents.

3. A method of performing a fibrinogen assay, comprising:
   (i) subjecting to an oscillating magnetic field a reaction slide bearing (1) a sample well for receiving a liquid sample, (2) a reaction chamber, and (3) a conduit means situated between said sample well and said reaction chamber and being in fluid communication therewith;
   said reaction chamber containing a dry reagent matrix comprising ecarin, in which is embedded a plurality of magnetic particles distributed homogeneously therethrough, wherein said dry reagent matrix is present only in said reaction chamber,
   (ii) under conditions suitable for conducting a fibrinogen assay, adding a volume of a whole blood or a blood-derived sample to said sample well, said volume of said sample being sufficient to substantially fill said conduit means without entering said reaction chamber or contacting said dry reagent matrix;
   (iii) adding a volume of buffer diluent and prothrombin to said sample well, said volume of said buffer being sufficient to wash said sample into said reaction chamber thereby causing said reagent to become solubilized and freeing the particles to move in an oscillating pattern induced by said oscillating magnetic field, wherein said oscillating pattern has a start time and a stop time, corresponding to a change in the degree of particle movement relative to said oscillating magnetic field,
   (iv) optically monitoring the oscillation of said magnetic particles to measure said start time and said stop time for the fibrinogen assay; and
   (v) using the start time and the stop time to correlate said start and stop time to the concentration of clottable fibrinogen in standard samples to measure the concentration of clottable fibrinogen in said whole blood or blood-derived sample.

4. A method of performing a clottable fibrinogen assay, comprising:
- (i) subjecting to an oscillating magnetic field a reaction slide bearing (1) a sample well for receiving a liquid sample and (2) a reaction chamber containing a dry reagent matrix comprising ecarin in which is embedded a plurality of magnetic particles distributed homogeneously therethrough,
- said sample well and reaction chamber being in fluid connection through a transport zone of geometry such that a volume of liquid analyte sample placed in said sample well and corresponding to the volume of said reaction chamber is transported from said sample well to said reaction chamber;
- (ii) under conditions suitable for conducting a fibrinogen assay, adding a whole blood or a blood-derived sample to said sample well whereby said sample is introduced into said reaction chamber, said reagent is solubilized and said particles are freed to move in an oscillating pattern induced by said oscillating magnetic field, wherein said oscillating pattern has a start time and a stop time, corresponding to a change in the degree of particle movement relative to said oscillating magnetic field,
- (iii) optically monitoring said reaction chamber to provide a particle oscillation curve and to measure a maximum amplitude of said particle oscillation, A, and a subsequent residual, post peak minimum amplitude, B, of said particle oscillation; and
- (iv) using at least B to correlate at least B to the concentration of clottable fibrinogen in standard samples to measure the concentration of clottable fibrinogen in said whole blood or blood-derived sample.

5. The method of claim 4, wherein only B is used to measure said fibrinogen concentration in said sample.

6. The method of claim 4, wherein a ratio A/B or B/A is used to measure said fibrinogen concentration in said sample.

7. The method of claim 4, wherein A−B is used to measure said fibrinogen concentration in said sample.

8. The method of claim 4, wherein (A−B)/A or A/(A−B) is used to measure said fibrinogen concentration in said sample.

9. The method of claim 4, wherein A/B and (A−B)/A are used to measure said fibrinogen concentration of said sample.

10. The method of claim 4, wherein the slope of the oscillation curve taken at a region between A and B is used to determine fibrinogen concentration of said sample.

11. The method of claim 4, wherein the area either above or below the oscillation curve as defined by the region between A and B or a portion thereof is used to determine fibrinogen concentration of said sample.

12. The method of claim 4, wherein said dry reagent further comprises at least one member selected from the group consisting of buffers and binding agents.

13. A method of performing a fibrinogen assay, comprising:
- (i) subjecting to an oscillating magnetic field a reaction slide bearing (1) a sample well for receiving a liquid sample, (2) a reaction chamber, and (3) a conduit means situated between said sample well and said reaction chamber and being in fluid communication therewith; said conduit means containing a dry reagent matrix comprising ecarin in which is embedded a plurality of magnetic particles distributed homogeneously therethrough, wherein said dry reagent is present only in said conduit,
- (ii) under conditions suitable for conducting a fibrinogen assay, adding a whole blood or blood-derived sample to said sample well, the volume of said sample being sufficient to substantially fill said conduit means and reaction chamber and to mix with said reagent and wash said reagent into said reaction chamber thereby freeing said magnetic particles to move in an oscillating pattern induced by said oscillating magnetic field, wherein said oscillating pattern has a start time and a stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under the oscillation curve,
- (iii) optically monitoring said reaction chamber to measure one or more of the following parameters (iiia) said start time and said stop time for said fibrinogen assay, or (iiib) a maximum amplitude of said particle oscillation, A, and a subsequent residual, post peak minimum amplitude, B, of said particle oscillation, or (iiic) a slope of said particle oscillation curve or area defined by said curve in the region between A and B; and
- (iv) using said start time and said stop time, or at least B, or said slope, or said area to correlate at least one of said parameters (iiia)–(iiic) to the concentration of clottable fibrinogen in standard samples to measure the concentration of clottable fibrinogen in said whole blood or blood-derived samples.

14. The method of claim 13, wherein, before step (ii), a volume of distilled water is added to said sample well, sufficient to be taken into said conduit via capillary action thereby solubilizing said dry reagent and freeing said magnetic particles prior to the addition of said whole blood or said blood-derived sample.

15. A method for performing a fibrinogen assay, comprising:
- (i) under conditions suitable for conducting a fibrinogen assay, adding a whole blood or blood-derived sample to a sample well of a reaction slide, said reaction slide bearing (1) said sample well for receiving a liquid sample, (2) a reaction chamber, and (3) a conduit means situated between said sample well and said reaction chamber and being in fluid communication therewith;
- said conduit means containing a dry reagent matrix comprising ecarin in which is embedded a plurality of magnetic particles distributed homogeneously therethrough, wherein said dry reagent matrix is present only in said conduit,
- wherein the volume of said whole blood or said blood-derived sample added to said sample well is sufficient to substantially fill said conduit means and said reaction chamber and to wash said reagent into said reaction chamber thereby freeing said magnetic particles;
- (ii) subjecting said reaction slide to an oscillating magnetic field either at the time of addition of said whole blood or said blood-derived sample to said sample well or shortly thereafter, wherein said oscillating magnetic field causes said freed magnetic particles to move in an oscillating pattern, wherein said oscillating pattern has a start time and a stop time, corresponding to a change in the degree of particle movement relative to said oscillating magnetic field, and (iii) optically monitoring said reaction chamber to provide a particle oscillation curve and to measure one or more of the following parameters (iiia) at least a post peak minimum amplitude of said magnetic particle oscillation, (B), or (iiib) a slope of said particle oscillation curve, or (iiic) an area defined by the particle oscillation curve between a maximum amplitude of said particle oscillation, A, and B, to correlate at least one of said parameters (iiia)–(iiic) to the concentration of clottable fibrinogen in standard samples to measure the concentration of clottable fibrinogen in said whole blood or blood-derived sample.

16. A method of performing a quantitative fibrinogen assay, comprising:

(i) contacting a dry reagent matrix, comprised of ecarin and in which is homogeneously embedded a plurality of magnetic particles, contained in a reaction chamber and subjected to a rotating magnetic field generated by a process comprising spinning a north pole and a south pole of a magnetic field about a central point, with an amount of a diluted blood sample sufficient to fill said reaction chamber, thereby freeing said magnetic particles to move under the influence of the rotating magnetic field;

(ii) optically monitoring the response of said magnetic particles to said rotating magnetic field, during clotting of said blood sample, generating a response curve relating clotting time to fibrinogen concentration;

(iii) determining a clotting time endpoint from said response curve; and (iv) comparing the clotting time endpoint from step (iii) to a stored standard calibration curve relating clotting time endpoint to fibrinogen content, prepared with samples of known fibrinogen content, to determine the amount of clottable fibrinogen in the sample.

17. A method of performing a fibrinogen assay according to claim 16, wherein said diluted blood sample is diluted whole blood.

18. A method of performing a fibrinogen assay according to claim 17, wherein said diluted whole blood further comprises an anticoagulant.

19. A method of performing a fibrinogen assay according to claim 16, wherein said diluted blood sample is diluted plasma.

20. An apparatus for performing a fibrinogen assay comprising:

(i) a reaction slide bearing a sample well for receiving a liquid sample and a reaction chamber containing a dry reagent matrix comprising ecarin and in which is embedded a plurality of magnetic particles distributed homogeneously therethrough, said sample well and reaction chamber being in fluid connection through a transport zone of geometry such that a volume of liquid analyte sample placed in said sample well and corresponding to the volume of said reaction chamber is transported from said sample well to said reaction chamber;

(ii) means for providing a magnetic field selected from the group consisting of a rotating magnetic field and an oscillating magnetic field; and (iii) an optical detection means for detecting a response of said magnetic particles to said magnetic field.

21. An apparatus for performing a fibrinogen assay according to claim 20, wherein said liquid analyte sample is diluted whole blood.

22. An apparatus for performing a fibrinogen assay according to claim 21, wherein said diluted whole blood further comprises an anticoagulant.

23. An apparatus for performing a fibrinogen assay according to claim 20, wherein said liquid analyte sample is diluted plasma.

24. In a fibrinogen assay wherein a whole blood or blood-derived sample is contacted with a fibrinogen assay reagent to cause formation of a fibrin clot which is correlated to content of fibrinogen in the whole blood or blood-derived sample, the improvement wherein the fibrinogen assay reagent comprises ecarin as active clot-inducing agent.

25. The fibrinogen assay of claim 24, wherein said fibrinogen assay reagent is a dry chemistry reagent.

26. The fibrinogen assay of claim 24, wherein said fibrinogen assay reagent is a liquid reagent.

27. A reaction slide for performing a fibrinogen assay, comprising:

a sample well for receiving a liquid sample and a reaction chamber containing a dry reagent matrix comprising ecarin and in which is embedded a plurality of magnetic particles distributed homogeneously therethrough, said sample well and reaction chamber being in fluid connection through a transport zone of geometry such that a volume of liquid analyte sample placed in said sample well and corresponding to the volume of said reaction chamber is transported from said sample well to said reaction chamber.

28. The reaction slide of claim 27, wherein said dry reagent matrix further comprises one or more members selected from the group consisting of buffers and lyophilization stabilizers.

* * * * *